US006538741B2

(12) United States Patent
Celotti et al.

(10) Patent No.: US 6,538,741 B2
(45) Date of Patent: Mar. 25, 2003

(54) METHOD TO EVALUATE THE QUALITY OF GRAPES AND RELATIVE DEVICE

(75) Inventors: Emilio Celotti, Udine (IT); Giuseppe Carcereri De Prati, Colognola ai Colli (IT)

(73) Assignee: Università Degli Studi di Udine, Udine (IT)

(*) Notice: Subject to any disclaimer, the term of this patent is extended or adjusted under 35 U.S.C. 154(b) by 0 days.

(21) Appl. No.: 10/016,780

(22) Filed: Oct. 26, 2001

(65) Prior Publication Data
US 2002/0048021 A1 Apr. 25, 2002

Related U.S. Application Data

(63) Continuation of application No. PCT/IB00/00514, filed on Apr. 25, 2000.

(30) Foreign Application Priority Data
Apr. 28, 1999 (IT) .......................................... UD99A0086

(51) Int. Cl.[7] .................................................. G01J 3/46
(52) U.S. Cl. ........................ 356/402; 356/356; 356/405
(58) Field of Search ................................ 356/402, 405, 356/409, 410

(56) References Cited

U.S. PATENT DOCUMENTS

| 3,992,109 A | * 11/1976 | Bock ............................. 356/181 |
| 3,998,551 A | * 12/1976 | Suga .............................. 356/73 |
| 5,679,955 A | 10/1997 | Schmidt et al. |
| 5,825,478 A | 10/1998 | Wilcox et al. |

FOREIGN PATENT DOCUMENTS

WO    WO95/21242 A1    8/1995

OTHER PUBLICATIONS

E. Lanza and B.W. Li : "Application for Near Infrared Spectroscopy for Predicting the Sugar Content of Fruit Juices" Journal of Food Science, vol. 49, 1984, pp. 995–998.*

F.M. Clydesdale ("Continuous Colorimetry" Instrumentation in the Food and Beverage Industry, Univ. of Massachusetts, USA, vol. 2, pp. 33–43, 1973.*

F.M. Clydesdale, "Continuous Colorimetry" *Instrumentation In The Food And Beverage Industry* (Univ. Of Massachusetts, USA), vol. 2, pp. 33–43, (1973).

E. Lanza et al., "Application for Near Infrared Spectroscopy for Predicting the Sugar Content of Fruit Juices", *Journal of Food Science*, vol. 49, pp. 995–998, (1984).

J. Koch et al., "Zum Nachweis von verfälschten Orangensäften" *Deutsche Lebensmittel–Rundschau*, vol. 6, pp. 185–195, (1971).

* cited by examiner

*Primary Examiner*—Frank G. Font
*Assistant Examiner*—Roy M. Punnoose
(74) *Attorney, Agent, or Firm*—Akin, Gump, Strauss, Hauer & Feld, L.L.P.

(57) ABSTRACT

Method and device to evaluate the quality of grapes, comprising a step to evaluate the presence and percentage of coloring substances in the juice by means of emitting an optical signal through the sample of juice, with the consequent monitoring of a significant calorimetric parameter, and a step to correlate the percentage of coloring substances in the sample with a defined quality and commodity class of said grapes from which the juice is obtained.

16 Claims, 2 Drawing Sheets

US 6,538,741 B2

METHOD TO EVALUATE THE QUALITY OF GRAPES AND RELATIVE DEVICE

CROSS-REFERENCE TO RELATED APPLICATION

This application is a Continuation of International Application No. PCT/IB00/00514, filed Apr. 25, 2000, which was published in the English language on Nov. 9, 2000 under International Publication No. WO 00/66986 and the disclosure of which is incorporated herein by reference.

FIELD OF THE INVENTION

This invention concerns a method to evaluate the quality of grapes.

The invention also concerns the device suitable to achieve the method.

The invention is applied mostly, but not exclusively, in the field of wine-making, to perform a rigorous and selective evaluation of the quality of a sample of grape juice in order to discriminate the quality level of the grapes from which the juice has been obtained, and to allow it to be classified according to its actual polyphenol composition and characteristics.

BACKGROUND OF THE INVENTION

In the state of the art, and in the field of evaluating the quality of grape juice obtained from a particular batch of grapes, and/or of the grapes themselves from which the juice comes, the most commonly used procedure at present provides to analyse the sugar content of the sample.

This procedure is sometimes integrated, or more rarely replaced, by an analysis of the titratable acidity of the sample, in order to obtain further information and to allow to classify the sample more reliably and more rigorously into a certain class of commodity.

However, analysing the titratable acidity requires equipment which is not always available and times which are sometimes not compatible with the requirements of the producing companies.

Moreover, the factors which determine the quality of the grapes, and in general of fruit and vegetable juices, are not limited only to the presence and percentage of sugars and/or acids dissolved in the juice; they are also linked to the presence of particular substances, mainly such as polyphenolic substances and aromatic substances.

At present, however, the percentage of these substances in the grapes is never quantified when the technological procedures to transform the grapes into wine are begun.

Therefore, the commodity classification of the various qualities of grapes is not rigorous and does not give an efficient, selective and objective discrimination into a plurality of quality levels according to the actual composition characteristics of the juices obtained from the various batches of grapes.

Various solutions have been proposed in the state of the art which exploit a colorimetric analysis of a juice, usually carried out with sources of light operating in the region of infra-red, in order to determine some characteristics thereof.

For example, the article "Continuous Colorimetry" by F. M. Clydesdale, taken from the journal "Instrumentation in the Food and Beverage Industry", vol. 2, 1973, pages 33–43, describes a method of spectrophotometric analysis made on a plurality of samples of blueberry juice in order to verify the content of colored pigments in said samples.

The purpose of the analysis is to select, in an analytical manner, samples of juice which answer desired visual criteria of color.

This document does not teach to construct quality classes of the product from which the juice is obtained according to calorimetric analyses.

The article "Application for Near Infrared Spectroscopy for Predicting the Sugar Content of Fruit Juices", taken from the Journal of Food Science, vol. 49, 1984, pages 995–998 describes a method of spectrophotoscopic analysis to analytically find the content of sugars in juice.

In this case too there is no reference to a classification of the basic food product according to the calorimetric analysis.

The document WO-A-95/21242 describes a method to determine the colors of beer, and its level of bitterness, by illuminating the beer with a light of a particular wavelength, causing its iso-$\alpha$-acids to fluoresce, monitoring the level of fluorescence and comparing it with known reference parameters.

This document does not teach a method to classify a food product made of juice either.

Moreover, none of the known solutions provides to integrate the color data with existing instruments, for example with those which monitor the sugar level of the juice.

The present Applicant has devised and embodied this invention to overcome these shortcomings in an economical, functional and extremely practical manner.

SUMMARY OF THE INVENTION

The invention is set forth and characterized in the respective main claims, while the dependent claims describe other characteristics of the idea of the main embodiment.

The purpose of the invention is to achieve a method, and relative device, suitable to perform an objective evaluation of the quality of a grape juice so as to allow the selective discrimination of a plurality of quality levels relating to the basic product from which the juice is obtained according to the actual composition characteristics of the said juice.

A further purpose is to achieve a device suitable to perform this quality evaluation which is economical, practical and compatible with existing equipment.

According to the invention, the method to evaluate the quality of juices, obtained from grapes, provides to evaluate the presence and percentage of coloring substances in the juice by means of emitting an optical signal which passes through the sample of juice and then to monitor a significant calorimetric parameter.

To be more exact, the invention provides to emit a beam of light directed towards the sample of juice to be analysed, to receive the optical signal transmitted through this sample, and to process the optical signal received to acquire information relating to the presence and percentage of coloring substances.

According to the presence and percentage of these coloring substances, the invention provides to construct an analytical classification of the basic fruit or vegetable product to sub-divide said grapes, into a plurality of quality classes.

In a preferential embodiment, the device which achieves the method according to the invention comprises:

a source of light associated with a fiber-optic transmission mean, or guide, suitable to convey the beam of light through the sample of juice to be analysed, a reception element consisting of a fiber-optic spectrometer suitable to measure the transmittance or absorbance of the juice to be analysed, and a processing unit, equipped with specific software, suitable to receive the information relating to the optical parameters taken from the reception element and to supply the estimation of the content of coloring substances in the juice, from which the phenol quality of the basic fruit or vegetable product can be found.

The use of a fiber-optic source is not absolutely necessary to achieve the invention, but it is preferential, since it guarantees that the analysis is immediate and therefore the results are too.

In one embodiment of the invention, the source of light consists of a tungsten lamp and the fiber-optic spectrometer is suitable to discriminate light signals at least in the range of frequencies between 190 nm and 850 nm, that is, substantially in the field of the visible and the ultraviolet.

According to the signal received and its position in the spectrum of frequencies discriminated by the fiber-optic spectrometer, the processing unit is able to quantify the content of coloring substances (for example the anthocyanins, or the red and/or yellow polymers) contained in the grape juice, and consequently is able to classify the basic product, for example the grapes, into a defined quality and commodity level.

By means of this evaluation criterion, which can integrate or replace the procedures of sugar or acid classification which are already used, it is possible to discriminate grapes or other fruit and vegetable products more rigorously and selectively than happens in the state of the art. It is therefore possible to devise a scale comprising a plurality of quality levels inside which the various products from which the juices analysed are obtained can be placed according to their content in terms of coloring substances.

In a preferential embodiment, the device which achieves the calorimetric evaluation of the grapes is integrated into the existing equipment suitable to carry out the analysis of the sugar content of the juice.

BRIEF DESCRIPTION OF THE DRAWINGS

The attached Figures are given as a non-restrictive example and show a preferential embodiment of the invention as follows.

DETAILED DESCRIPTION OF PREFERRED EMBODIMENT

Figure 1:
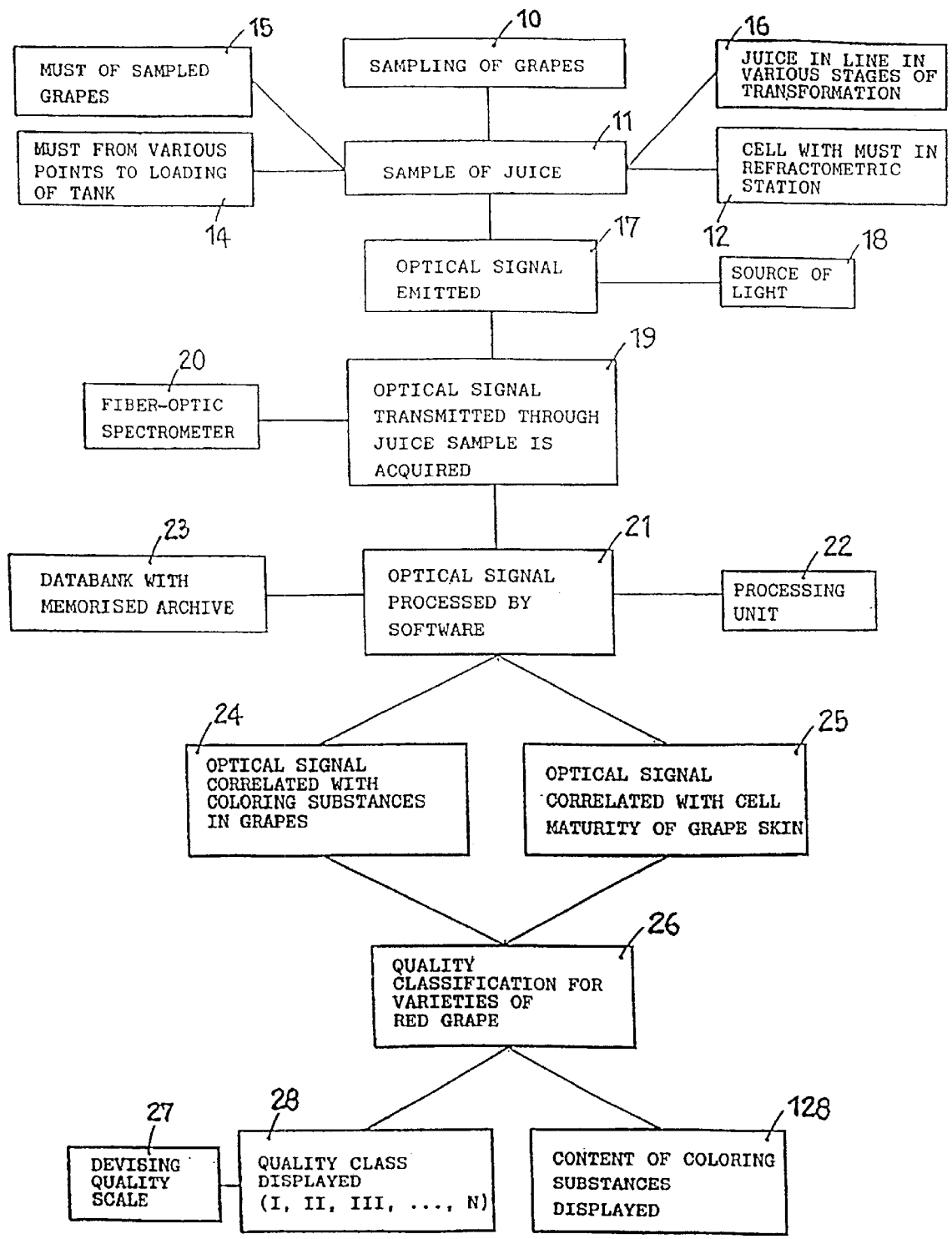
FIG. 1 is a block diagram of the method according to the invention.

With reference to FIG. 1, a method to evaluate the quality of grape juice according to the invention provides a first step 10 to select the sample of grapes to be analysed, followed by a step 11 to obtain the sample of juice on which the calorimetric analysis is made.

The sample of juice can be subjected to the calorimetric analysis at a desired step in the process of transforming the juice.

For example, the must can be analysed when it is in the cell 12 of the refractometric station 13 where the sugar analysis is carried out, or during the step 14 when it is loaded into the tanks, or again it is possible to analyse the must obtained after a procedure 15 of sampling the grapes. According to another embodiment, the calorimetric analysis is made on the juice at any intermediate step 16 whatsoever during its transformation.

According to the invention, the method provides a step 17 to emit an optical signal through the sample of juice to be analysed by means of a suitable source of light 18, and a step to acquire 19 the optical signal transmitted through the sample of juice.

The acquisition step is made, in this case, by means of a fiber-optic spectrometer 20 suitable to measure a significant calorimetric parameter, such as the absorbance and/or transmittance of the sample of juice analysed.

The optical signal acquired by the spectrometer 20 is subjected to a processing procedure 21, made by a processing unit 22 equipped with the specific software.

The processing unit 22 is associated with or incorporates a data bank 23 containing a memorized archive which holds a plurality of correlation parameters, for example obtained experimentally, which correlate the optical and calorimetric parameters acquired on the sample analysed with the organic and composition characteristics of the sample of grapes analysed.

For example, this processing allows to follow a procedure 24 of correlating the optical signal acquired with the presence and percentage of the coloring substances, for example the anthocyanins or the red and/or yellow polymers, in the juice; or it allows to follow a procedure 25 of correlating the optical signal with the cell maturity of the grape skins.

The processing of the optical signal by the processing unit 22 thus allows to achieve a quality classification 26 of the grapes, and possibly also of the relative juice, based on the actual organic and composition characteristics thereof.

By means of a prior procedure 27 of devising a quality scale, suitable to associate a specific class to a determined percentage range of coloring substances in the juice, the processing unit 22 can follow a display procedure 28 by means of which the quality class to which the grapes from which we have obtained the specific sample of juice analysed belongs is identified and displayed.

The display 128 of the percentage and/or absolute content of coloring substances in the specific sample of juice may also be provided.

Figure 2:
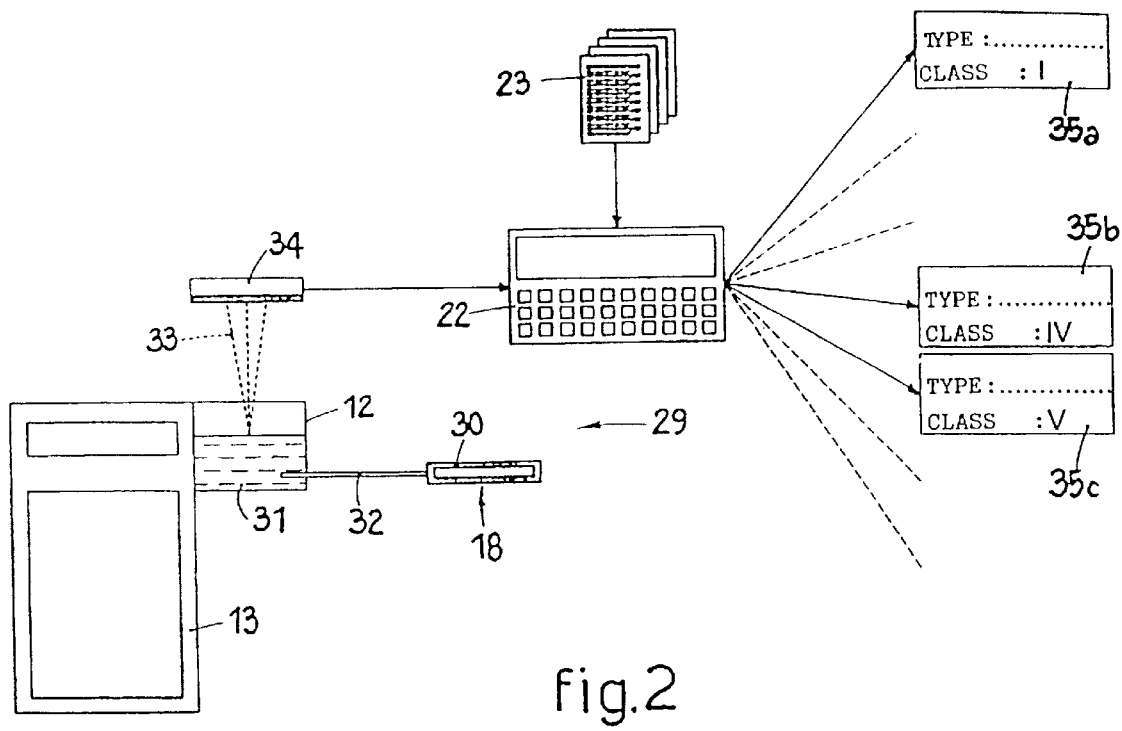
FIG. 2 is a schematic view of a device suitable to achieve the method according to the invention.

The diagram shown in FIG. 2 shows the example of the case where the quality analysis made by monitoring an optical signal transmitted through a sample of juice is made on a cell 12 associated with the refractometric station 13 in which the analysis is made of the sugar content of the juice.

This embodiment is extremely practical and economical since it exploits most of the equipment already existing and used for quality analysis of the grape juice.

In this case, the device 29 suitable to achieve the analysis comprises a source of light 18, for example consisting of a tungsten lamp 30, suitable to emit a beam of light which is channeled into a guide 32 and sent inside the cell 12 containing the sample of juice 31 to be analysed.

The optical signal 33 monitored after it has passed through the juice 31, which can be channeled through the same guide 32 or by means of another suitable conductor, is acquired by a fiber-optic spectrometer 34 suitable to monitor the characteristic optical parameters, such as for example its transmittance and/or absorbance, and sent to the processing unit 22.

According to the data supplied by the memorized archive 23, the processing unit 22 is able to classify the juice analysed according to the composition characteristics and to construct a quality classification of the initial grapes with a desired number of quality levels established in advance.

The processing unit 22 is thus suitable to display the quality class 35a, 35b, 35c . . . (in this case from I to V) corresponding to the specific type of grape or juice analysed.

Figure 3A:
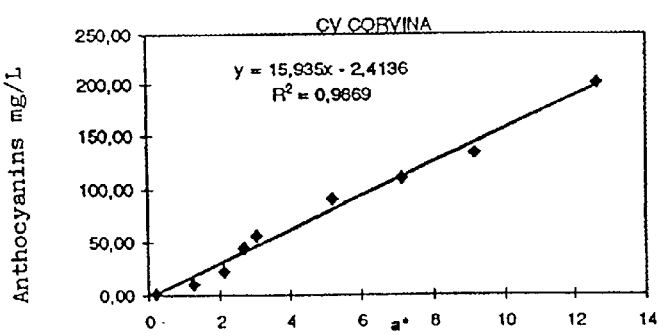
FIGS. 3a and 3b show two experimental graphs relating to the correlations between a colorimetric parameter monitored by means of the method according to the invention and the presence of coloring substances in the grapes from which the sample of juice analysed is obtained.
Figure 3B:
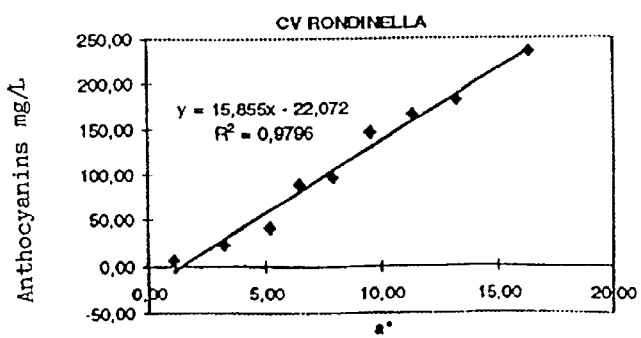

The graphs given as examples in FIGS. 3a and 3b, obtained experimentally, show the correlation between the calorimetric parameter a*, relating to the color quality of the optical signal, and the percentage of anthocyanins present in the grapes, expressed in milligrams per liter, examined for two different types of grape, respectively Corvina and Rondinella.

Processing the optical signal 33 by means of fiber-optic monitoring hence allows to classify the sample of grape according to the actual content of coloring substances, and therefore to classify the sample qualitatively, associating a quality level of the initial grapes to every percentage quantity range of these substances in the juice.

What is claimed is:

1. A method for evaluating the quality of grapes comprising the steps of:

acquiring optical and calorimetric parameters of a sample of grape juice by emitting an optical signal and passing the optical signal through the sample of grape juice, wherein the sample of grape juice is obtained by pressing a sample of the grapes;

detecting the optical and colorimetric parameters;

correlating the detected optical and colorimetric parameters with correlation parameters previously stored in a memorized archive, the correlation parameters relating the optical and colorimetric parameters with organic and compositional characteristics of the sample of grapes, the organic and compositional characteristics including characteristics of color substances;

determining a content of the coloring substances in the sample of grape juice;

determining phenolic characteristics of the sample of grape juice based on the content of the coloring substances; and correlating a specific percentage content of the coloring substances with a defined and univocal quality and commodity class of the sample of the grapes.

2. The method of claim 1, wherein the sample of grape juice is obtained from the sample of the grapes obtained from just pressed grapes.

3. The method of claim 1, wherein the step of detecting the at least one of the optical and calorimetric parameter comprises receiving the optical signal with a fiber-optic spectrometer, processing the optical signal with a processing unit to evaluate the percentage value of said coloring substances in the sample of grape juice, and defining and displaying the quality and commodity class of the sample of grapes.

4. The method of claim 1, wherein said emission of the optical signal is performed in line on the sample of grape juice obtained during the process of transforming said grape juice.

5. The method of claim 1, wherein said emission of the optical signal is performed in line on the sample of grape juice contained in a cell predisposed for sugar analysis, or in the step of loading said sample of grape juice into a tank.

6. The method of claim 1, wherein said coloring substances are anthocyanins.

7. The method of claim 1, wherein said coloring substances are red or yellow polymers.

8. The method of claim 1, wherein said at least one of the optical and colorimetric parameter is transmittancy.

9. The method of claim 1, wherein said at least one of the optical and colorimetric parameter is absorbance.

10. The method of claim 1, further comprising the step of devising a quality scale which associates a specific quality and commodity class of a fruit or a vegetable product to a predetermined percentage range of the coloring substances.

11. A device to evaluate the quality of grapes, comprising:

means to emit and transmit a beam of light through a sample of grape juice obtained by pressing a sample of the grapes;

reception means suitable for measuring at least one of an optical and colorimetric parameter characteristic of said sample of grape juice and;

a processing means suitable for receiving information relating to said at least one of the optical and calorimetric parameter measured, to supply an estimate of a percentage content of coloring substances in said sample of grape juice and to correlate said percentage content to a defined quality and commodity class of said sample of grapes, said processing means comprising a processing unit associated at least with a data bank comprising a memorized archive of parameters of correlation between said at least one of the optical and calorimetric parameter measured and the percentage content of the coloring substances in the sample of grape juice with organic and composition characteristics of the sample of the grapes, said organic and composition characteristics comprising phenolic characteristics of the sample of the grapes.

12. The device of claim 11, wherein said means to emit the beam of light comprises a tungsten lamp.

13. The device of claim 11, wherein said means to transmit the beam of light comprises a fiber-optic guide.

14. The device of claim 11, wherein said reception means comprises a fiber-optic spectrometer.

15. The device of claim 11, wherein said fiber-optic spectrometer is suitable for discriminating frequencies in a range of between 190 nm and 850 nm.

16. The device of claim 11, wherein the device is suitable for integrating into a refractometric station which analyzes sugar content of the sample of grape juice.

* * * * *